US009884307B2

(12) United States Patent
Matoga

(10) Patent No.: US 9,884,307 B2
(45) Date of Patent: Feb. 6, 2018

(54) MOF-TYPE LAYERED COORDINATION POLYMERS OF MANGANESE, METHOD OF THEIR PREPARATION, MODIFICATION AND USE THEREOF

(71) Applicant: UNIWERSYTET JAGIELLOŃSKI, Kraków (PL)

(72) Inventor: Dariusz Matoga, Siepraw (PL)

(73) Assignee: Uniwersytet Jagiellonski, Krakow (PL)

( * ) Notice: Subject to any disclaimer, the term of this patent is extended or adjusted under 35 U.S.C. 154(b) by 94 days.

(21) Appl. No.: 14/915,295

(22) PCT Filed: Sep. 2, 2014

(86) PCT No.: PCT/PL2014/050052
§ 371 (c)(1),
(2) Date: Feb. 29, 2016

(87) PCT Pub. No.: WO2015/030617
PCT Pub. Date: Mar. 5, 2015

(65) Prior Publication Data
US 2016/0214080 A1   Jul. 28, 2016

(30) Foreign Application Priority Data
Sep. 2, 2013 (PL) .......................................... 405228

(51) Int. Cl.
*B01J 20/22* (2006.01)
*C07C 63/307* (2006.01)
(Continued)

(52) U.S. Cl.
CPC ............. *B01J 20/226* (2013.01); *C01B 31/20* (2013.01); *C07C 63/307* (2013.01); *C07D 213/79* (2013.01); *C07D 213/803* (2013.01)

(58) Field of Classification Search
CPC ...... B01J 20/226; C01B 31/20; C07C 63/307; C07D 213/79; B01D 2253/204
(Continued)

(56) References Cited

U.S. PATENT DOCUMENTS

2009/0143595 A1* 6/2009 James ................... C07C 51/418
546/327
2012/0118153 A1* 5/2012 Omary ................... B01D 53/02
95/143

(Continued)

FOREIGN PATENT DOCUMENTS

WO   2007023295 A2   3/2007

OTHER PUBLICATIONS

Wei et al. "A manganese metal-organic framework which remains crystalline on desolvation, and which gives insight into the rotational freedom of framework aromatic groups" (2004) Microporous and Mesoporous Materials 73, 97-100.*

(Continued)

*Primary Examiner* — Frank Lawrence
(74) *Attorney, Agent, or Firm* — Kilyk & Bowersox, P.L.L.C.

(57) ABSTRACT

The invention solves the problem of the development of microporous layered MOF-type manganese materials based on isonicotinate anions, their synthesis and modification with selected ionic substances and application associated with the adsorption of the molecules and the construction of solid superionic conductors.

18 Claims, 5 Drawing Sheets

(51) Int. Cl.
  *C01B 31/20* (2006.01)
  *C07D 213/79* (2006.01)
  *C07D 213/803* (2006.01)
(58) Field of Classification Search
  USPC .......... 95/90, 116, 139, 140, 143, 900, 902; 502/400
  See application file for complete search history.

(56) References Cited

U.S. PATENT DOCUMENTS

2014/0190436 A1* 7/2014 Inubushi ................ B01D 53/02
                                                           123/1 A
2016/0176070 A1* 6/2016 James .................... C07F 15/06
                                                           546/7

OTHER PUBLICATIONS

International Search Report and Written Opinion issued in corresponding International Patent Application No. PCT/PL2014/050052 dated Apr. 23, 2015 (8 pages).
Pichon et al., "Solvent-free synthesis of a microporous metal-organic framework," The Royal Society of Chemistry, CrystEngComm, vol. 8, 2006, pp. 211-214.

* cited by examiner

MOF-TYPE LAYERED COORDINATION POLYMERS OF MANGANESE, METHOD OF THEIR PREPARATION, MODIFICATION AND USE THEREOF

This application is a National Stage Application of PCT/PL2014/050052, filed Sep. 2, 2014, which claims priority to Polish Patent Application No. P405228, filed Sep. 2, 2013.

The present invention provides new MOF-type layered coordination polymers of manganese, the method of their preparation, modification and use thereof. These polymers and the products of their modification with other substances are applied to detecting, capture and storage of various molecules, for example: hydrogen, carbon dioxide, carbon oxide, alcohols, water, hydrocarbons as well as for building systems using superionic and ionic-electronic conductors.

In recent years design and synthesis of porous coordination polymers also called metal-organic frameworks (MOFs) is one of the most intensively developing areas of materials chemistry and nanotechnology ((a) *Chem. Rev.* 2012, 112, 673-1268. (b) *Chem. Soc. Rev.* 2011, 40, 453-1152).

MOF-type systems are crystalline materials (molecular sponges) made of two components: metal ions and organic molecules called linkers or bridges. Both components have tremendous impact on the structure and properties of the material. The wide range of their practical application is mainly due to large inner surface areas and flexibility. At the same time MOF materials exhibit high mechanical and thermal stability. These properties of MOF materials result in the possibility of adsorption of various "guests" molecules, which translates into a multiple use of MOF materials including, inter alia hydrogen and other gases storage, molecular identification, mixtures separation (by selective sorption), catalysis, synthesis, and adsorption of drugs.

Depending on the behavior of the framework after removal of the "guests" molecules, MOF-type systems have been divided into three groups: ((a) Kitagawa, S.; Uemura, K. *Chem. Soc. Rev.* 2005, 34, 109-119. (b) Uemura, K.; Matsuda, R.; Kitagawa, S. *J. Solid State Chem.* 2005, 178, 2420. (c) Kitagawa, S.; Kondo, M. *Bull. Chem. Soc. Jpn.* 1998, 71, 1739). The latest group consists of third generation systems characterized by flexible (dynamic) frameworks, which reversibly react to external stimuli such as: the presence of "guests" molecules, light or the change in electric field or temperature. The combination of the framework flexibility and the crystallinity of the third generation MOF systems opens opportunities to create unique properties not observed in conventional MOF-type materials ((a) Ferey, G.; Serre, C. *Chem. Soc. Rev.* 2009, 38, 1380. (b) Horike, S.; Shimomura, S.; Kitagawa, S. *Nat. Chem.* 2009, 1, 695).

In particular, MOFs are very interesting as new materials for carbon dioxide-greenhouse gas trapping, what is directly related to clean energy and environmental protection ((a) Zhang, Z. Zhao, Y.; Gong, Q.; Li, Z.; Li, J. *Chem. Commun.* 2013, 49, 653. (b) Sumida, K.; Rogow, D. L.; Mason, J. A.; McDonald, T. M.; Bloch, E. D.; Herm, Z. R.; Bae, T.-H.; Long, J. R. *Chem. Rev.* 2012, 112, 724. (c) Liu, J.; Thallapally, P. K.; McGrail, B. P.; Brown, D. R.; Liu, J. *Chem. Soc. Rev.* 2012, 41, 2308. (d) Li, J.-R.; Ma, Y.; McCarthy, M. C.; Sculley, J.; Yu, J.; Jeong, H.-K.; Balbuena, P. B.; Zhou, H.-C. *Coord. Chem. Rev.* 2011, 255, 1791). The main desirable features of these compounds are high sorption capacity and high capture selectivity of carbon dioxide over nitrogen. It has been observed that at high pressures large surface area of MOF materials facilitate their sorptive capacity, while at relatively low pressures a significant density of adsorption sites, such as coordinatively unsaturated metal centers with high affinity for carbon dioxide, is the key factor. The important role of such exposed metal centers in MOF systems has also been emphasized in the literature, in particular for manganese centers and the process of selective adsorption and catalysis ((a) Dincă M.; Dailly, A.; Liu, Y; Brown, C. M.; Neumann, D. A.; Long, J. R. *J. am. Chem. Soc.* 2006, 128, 16876. (b) Dincă M.; Yu, A. F.; Long, J. R. *J. Am. Chem. Soc.* 2006, 128, 8904. (c) Horike, S.; Dincă M.; Tamaki, K.; Long, J. R. *J. Am. Chem. Soc.* 2008, 130, 5854. (d) Qiu, L.-G.; Gu, L.-N.; Hu, G.; Zhang, L.-D. *J. Solid state Chem.* 2009, 182, 502. (e) Maji, T. K.; Pal, S.; Gurunatha, K. L.; Govindaraj, A.; Rao, C. N. R. *Dalton Trans.* 2009, 4426. (f) Han, Z.-B.; Lu, R.-Y; Zhou, Y-L.; Chen, Q.; Zeng, M.-H. *Inorg. Chem.* 2012, 51, 674. (g) Sumida, K.; Stuck, D.; Mino, L.; Chai, J.-D.; Bloch, E. D.; Zavorotynska, O.; Murray, L. J.; Dincă M.; Chavan, S.; Bordiga, S.; Head-Gordon, M.; Long, J. R. *J. Am. Chem. Soc.* 2013, 135, 1083).

Introduction or generation of open metal centers in MOF systems, in addition to organic linkers modification, is also an important strategy leading to improvements of carbon dioxide adsorption selectivity. The MOF-type systems based on manganese showing the selective adsorption of carbon dioxide over nitrogen are hardly known so far ((a) Jeong, E.; Lee, W R.; Ryu, D. W.; Kim, Y; Phang, W. J.; Koh, E. K.; Hong, C. S. *Chem. Commun.* 2013, 49, 2329. (b) Kar, P.; Halder, R.; Gomez-Garcia, C. J.; Ghosh, A. *Inorg. Chem.* 2012, 51, 4265. (c) Dybtsev, D. N.; Chun, H.; Yoon, S. H.; Kim, D.; Kim, K. *J. Am. Chem. Soc.* 2004, 126, 32).

Such metal-organic systems are described, for example, in U.S. Pat. No. 5,648,508, EP0790253, DE10111230, WO 2002/070526, WO 2007/101797 A, WO 2005/049484, WO 2006/089908, DE-A 10 2005 012 087, EP1928831 B1. The patent EP1928831 B1 describes the systems in which the role of coordination linkers is fulfilled by isonicotinate anions and Cu, Ni, Zn, Rh, Mn are metal centers.

Layered manganese systems, being the subject of the invention, contain isonicotinate anions as linkers between manganese nodes ($Mn_2$). Only a few other manganese compounds with isonicotinate anions, usually received in expensive solvothermal processes have been described in the literature ((a) Lee, W; Evans, O. R.; Yee, G. T.; *J. Solid state Chem.* 2000, 152, 152. (b) Hauptmann, R.; Kondo, M.; Kitagawa, S. *Z. Kristallogr.-New Cryst. Struct.* 2000, 215, 171. (c) Wei, Q.; Nieuwenhuyzen, M.; James S. L. *Microporous Mesoporous Mater.* 2004, 73, 97. (d) Huang, D.; Wang, W; Zhang, X.; Chen, C.; Chen, F.; Liu, Q.; Liao, D.; Li, L.; Sun, L. *Eur. J. Inorg. Chem.* 2004, 1454. (e) Yu, J. H.; Lu, J.; Xu, Y.; Zhang, X.; Xu, J.-Q. *Inorg. Chim. Acta* 2006, 359, 3205. (f) W. Dai, *Acta Crystallogr., Sect. E: Struct. Rep. Online*, 2008, 64, m1032). They were directly obtained from isonicotinic acid or aldehyde, and various salts of manganese(II) such as for example nitrates, perchlorates, chlorides.

Furthermore, for many years, intensive studies have been undertaken in search for materials, which, or on the basis of which better batteries, supercapacitors, fuel cells, etc. may be built. In particular, new solid electrolytes for lithium batteries are sought (Goodenough, J. B.; Park, K.-S. *J. Am. Chem. Soc.* 2013, 135, 1167).

Layered systems with easy-to-substitution sites are a good starting point for creating conductors by the introduction of ionic substances containing alkali metal cations (eg $Li^+$, $Na^+$, $K^+$).

The invention relates to new MOF-type layered manganese coordination polymers defined by the general formula 1:

$$\{[Mn_2(ina)_4(L)_x]\cdot yS\}_n$$

in which:
L is a neutral molecule of a solvent selected from the group consisting of $C_1$-$C_{12}$ alcohols or water, preferably water
S independently denotes inert solvent molecule selected from the group consisting of $C_1$-$C_{12}$ alcohols or water, preferably ethanol
x varies from 0 to 2; preferably 0 or 2 when L=water
y independently varies in the range from 0 to 4; preferably 0 or 2 when S=ethanol
n denotes a polymeric structure of the compound (two-dimensional network 2D).

Layered manganese systems, which are subject of the invention, belong to the third generation MOF systems. After removal of "guest" molecules, these systems contain coordinatively unsaturated manganese centers and selectively trap carbon dioxide versus nitrogen. They are suitable for modifications with the ionic substances as confirmed with the synthesis with ammonium thiocyanate.

Manganese compounds of the invention may be obtained by a new method according to the invention, which so far has not been described in the literature or disclosed in the patent applications. During the synthesis, one of the reactants (isonicotinic acid hydrazide) is converted by oxidation and/or hydrolysis into isonicotinate linker that forms a bridge between manganese centers. The direct use of isonicotinic acid under the same synthetic conditions does not lead to products of the invention. Other chemical compounds are formed in this process.

To obtain the manganese compounds according to the invention isonicotinic acid hydrazide (isoniazid) is condensed with lower ketones or aldehydes: aliphatic and/or aromatic ($C_1$-$C_6$) preferably acetone, under anaerobic or aerobic conditions, preferably in air. The condensation reaction of an aldehyde or ketone with isoniazid is carried out at 1:1 molar ratio or with a stoichiometric excess of one of the reactants. The reaction is carried out in a solvent which is a $C_1$-$C_{12}$ alcohol or aqueous-alcoholic solution, formed by mixing of $C_1$-$C_{12}$ alcohol and water in any ratio, preferably an aqueous-ethanolic solution. In the second stage, to prevent the deprotonation of the resulting hydrazide-hydrazone, an acidic substance is added into the system, preferably acetic acid, and a salt of manganese(II), preferably manganese(II) acetate hydrated or anhydrous. The reaction is carried out at a molar ratio 1:2:2 of manganese to isoniazid to the acid. The reaction can also be carried out with stoichiometric excess or a deficiency of manganese, as well as stoichiometric excess or a deficiency of acid. The reaction products precipitate spontaneously after a few days.

All steps in the synthesis are carried out in the temperature range from −130 to +260° C. and pressures in the range from 0.01 to 1 MPa, that is under temperature and pressure conditions, in which the reaction mixture is a solution or suspension, preferably in boiling point of the solvent at atmospheric pressure.

By suitable combinations of these parameters layered manganese coordination polymers $\{[Mn_2(ina)_4(L)_x]\cdot yS\}_n$ for which x≠0 and y≠0 are obtained with a good yield. The aforementioned synthesis of MOF materials may also result in a simultaneous formation of finely crystalline by-product. It can be easily separated from the main product via brief sonication of the mixture before filtering (ultrasonic cleaner), which results in crushing the grains of by-product and keeping the large crystals of the main product intact. Then, filtration is preferably performed using a fritted filter funnel of possibly high porosity (e.g. at least P2 (G2) type).

Systems, for which x=0 or y=0 (also=0 and y=0), are preferably obtained by removing the molecules L and/or S from the layered material obtained by the aforementioned method by heating ata temperature not exceeding 400° C. and/or under reduced pressure and/or the strong dehydrating agent ($P_4O_{10}$).

IR spectroscopy and powder X-ray diffraction have confirmed that the molecules L and S can be reversibly removed and re-incorporated (ie. obtained materials with L and S molecules according to the invention, form dynamic (elastic) metal-organic frameworks, which belong to the third generation MOF-type systems). Materials containing L and S molecules are stable in air, what is a great advantage in the case of MOF-type materials, because these materials often degrade in the presence of water. Total degradation of the material begins at a temperature above 400 degrees Celsius, which was confirmed by thermogravimetric analysis.

The advantages of the synthesis method according to the invention for the industrial production are:
processing under mild conditions, at relatively low temperatures, even at room temperature,
reproducibility: the synthesis have been carried out repeatedly, each time resulting in the same product,
scalability (the conditions for formation of 100 mg up to 1 kg in single synthesis have been checked so far),
starting materials are relatively cheap and easily available.

For comparison, MOF-type materials are often synthesized by solvothermal methods involving long-term heating of the mixture under high temperatures in autoclave and/or often in large quantities of relatively expensive and non-environmentally friendly (as compared with ethanol), high-boiling solvents such as, for example N,N-dimethylformamide.

Modifications of the manganese compounds with ionic substances using the method according to the invention are carried out by a mechanochemical method or in solution. Ionic substances used for modifications are compounds containing at least one anion from the group: halides (fluorides, chlorides, bromides, iodides), hydroxides, nitrates, sulfates and bisulfates, thiosulphates, phosphates and hydrophosphates, carbonates and bicarbonates, chlorates, bromates, iodates, thiocyanates, cyanides, cyanates, chromates and dichromates, silicates, arsenates, acetates, formates, oxalates, citrates, sulfides, hexafluorophosphates, tetrafluoroborates, tetraphenylborates; molybdates; tungstates; vanadates; phthalates and hydrogen phthalates; terephthalates, and containing at least one cation from the group: ammonium, alkylammonium, hydrogen, $Li^+$, $Na^+$, $K^+$.

In the case of mechanochemical method, the modification is carried out by grinding the starting layered MOF-type material with selected ionic substance in a mortar or a ball mill, without solvent or with small addition of solvent, preferably that which was used for the synthesis of the starting MOF material, in an amount of about 0-10 μl per 1 mg of solid reactants (liquid-assisted grinding method). At room temperature, grinding is preferably carried out in the time of 0-120 min. Grinding is carried out preferably at a molar ratio of starting material to the ionic substance in the range from 10:1 to 1:10. In the case of using the LAG method (liquid-assisted grinding method) grinding is carried out in the time specified above, wherein the solvent should also be removed (by evaporation which occurs during the grinding). As a solvent in the LAG method, preferably $C_1$-$C_{12}$ alcohol or aqueous-alcoholic solution formed by mixing in any ratio $C_1$-$C_{12}$ alcohol and water, is used.

In the case of the method in solution, modifications are carried out by mixing the MOF starting material with the ionic substance in a solvent such as: pyridine, N,N-dimethylformamide, N,N-diethylformamide N,N-dimethylacetamide, dimethyl sulfoxide, N-methylpyrrolidone, dimethyl carbonate, diethyl carbonate, $C_1$-$C_{12}$ alcohols, water, halogenated alkanes, acetonitrile, tetrahydrofuran or mixtures thereof. The reaction is carried out in a temperature range from −130 to 260° C. and the pressure range from 0.01 to 1 MPa, that is, under temperature and pressure conditions in which the reaction mixture is in the form of a solution or suspension. Most preferably, the reaction is carried out at the solvent boiling point or below, under atmospheric pressure.

The use of MOF-type layered materials in a way according to the invention includes detection/capture/storage of different molecules, such as $H_2$, $CO_2$, CO, alcohols, water, hydrocarbons. After activation (removal of molecules L and optionally S at increased temperature and/or vacuum) at about −60 degrees Celsius, the product selectively and reversibly binds $CO_2$, without binding $N_2$, NO; what may be applied in the selective removal of $CO_2$ from the exhaust gases (directly related to the environmental protection) or capturing of $CO_2$ in hermetic, confined spaces, where people are staying (for example during space flights, in submarines etc.) Reversible binding of $CO_2$, ethanol, n-butanol and the lack of interactions with $N_2$ and NO molecules has been confirmed for $\{[Mn_2(ina)_4(H_2O)_2].2EtOH\}_n$ after removal of $H_2O$ and EtOH (activation) by in situ FTIR spectroscopy and measurements of BET-$N_2$ adsorption isotherm. When the main MOF-type material is used to bind $CO_2$, after its activation, the presence of water is a disadvantage that may block the manganese centers, in which the $CO_2$ adsorption occurs. Thus, there is a need to remove water from the initial mixture (drying), from which carbon dioxide is removed.

Furthermore, the reversible and rapid binding of ethanol and water even at room temperature by the manganese layered systems can be applied to detect the presence of these compounds or for their separation. Manganese layered systems after activation (L and S removal) may act as sensors and monitoring of their condition may be carried out by IR and/or UV/vis spectroscopy.

The use of the MOF-type layered materials after their modification with ionic substances includes the construction of new superionic and ionic-electronic conductors. Their synthesis involves the introduction of ionic substances containing alkali metal cations (for example Li+, Na+, K+) into layered systems. These conductors may be used to design new batteries, supercapacitors or fuel cells.

X-ray analysis shows that the compounds of the invention are layered (2D) coordination polymers, wherein the layers are stabilized by hydrogen bonds involving L and S molecules (preferably water and ethanol, respectively). Isonicotinate anions play a role of $\mu_3$ and $\mu_2$ linkers in the lattice between dinuclear manganese clusters, interconnected by carboxylate bridges which form framework nodes (secondary building blocks) of (4,4) topology.

In the following detailed description, reference is made to the accompanying drawings, which form a part hereof, and in which is shown by way of illustration specific embodiments in which the invention may be practiced. The following detailed description, therefore, is not to be taken in a limiting sense, and the scope of the present invention is defined by the appended claims.

FIG. 1 shows the crystal structure of 2D $\{[Mn_2(ina)_4(H_2O)_2].2EtOH\}_n$ MOF. (a) Single layer with dinuclear $Mn_2$ nodes and their fourfold connectivity with isonicotinate linkers (EtOH guest molecules have been omitted) (left) viewed along the crystallographic a axis (H atoms omitted), and (right) represented in a spacefill model showing rectangular open channels. (b) Stacked layers viewed along the crystallographic c axis. (Left) Coordinated $H_2O$ molecules occupying the interlayer region and EtOH guest molecules are clearly visible. (Right) Sequence of interlayer hydrogen-bonds involving $H_2O$, EtOH and framework free oxygen atoms of carboxylate groups, is indicated as a line between atoms shown as balls.

Figure 4:
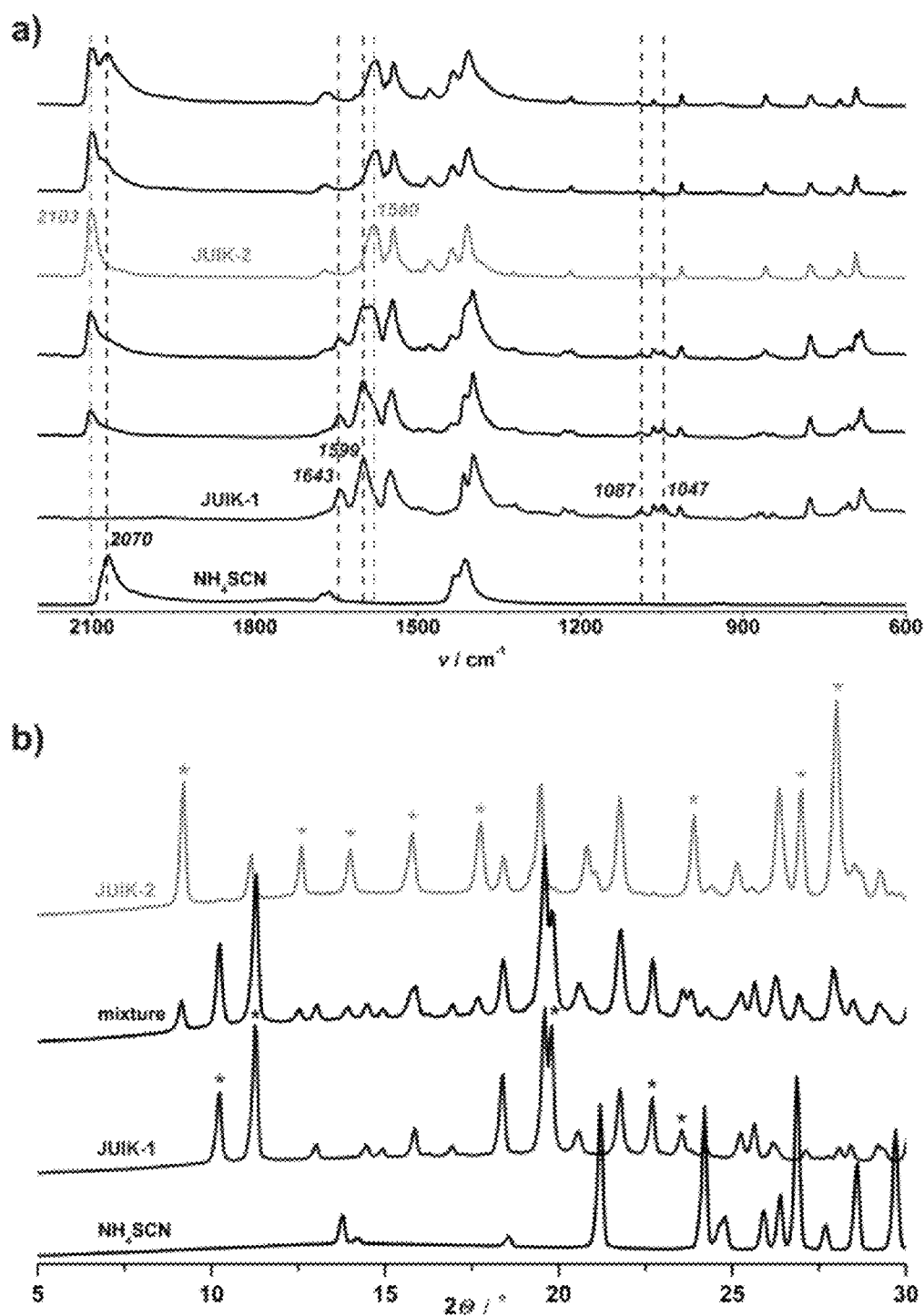

FIG. 4 shows $\{(NH_4)_2[Mn(ina)_4(SCN)_2]\}_n$ (JUIK-2) formation upon 5 min LAG (EtOH) grinding of $\{[Mn_2(ina)_4(H_2O)_2].2EtOH\}_n$ (JUIK-1) and $NH_4SCN$ at various stoichiometries (given as $\{[Mn_2(ina)_4(H_2O)_2].2EtOH\}_n$ to $NH_4SCN$ ratio). a) IR-ATR spectra of ground reactants (top to bottom): 1:3.5; 1:2.7; 1:2 (pure $\{(NH_4)_2[Mn(ina)_4(SCN)_2]\}_n$); 1:1; 1:0.5; initial $\{[Mn_2(ina)_4(H_2O)_2].2EtOH\}_n$; initial $NH_4SCN$. Dotted lines indicate selected wavenumbers of initial reactants and $\{(NH_4)_2[Mn(ina)_4(SCN)_2]\}_n$. b) PXRD patterns (top to bottom): 1:2 (pure $\{(NH_4)_2[Mn(ina)_4(SCN)_2]\}_n$); 1:0.5 (mixture of $\{(NH_4)_2[Mn(ina)_4(SCN)_2]\}_n$ and unreacted $\{[Mn_2(ina)_4(H_2O)_2].2EtOH\}_n$); initial $\{[Mn_2(ina)_4(H_2O)_2].2EtOH\}_n$; initial $NH_4SCN$. Characteristic reflections of $\{[Mn_2(ina)_4(H_2O)_2].2EtOH\}_n$ and $\{(NH_4)_2[Mn(ina)_4(SCN)_2]\}_n$ are labeled "*".

Figure 5:
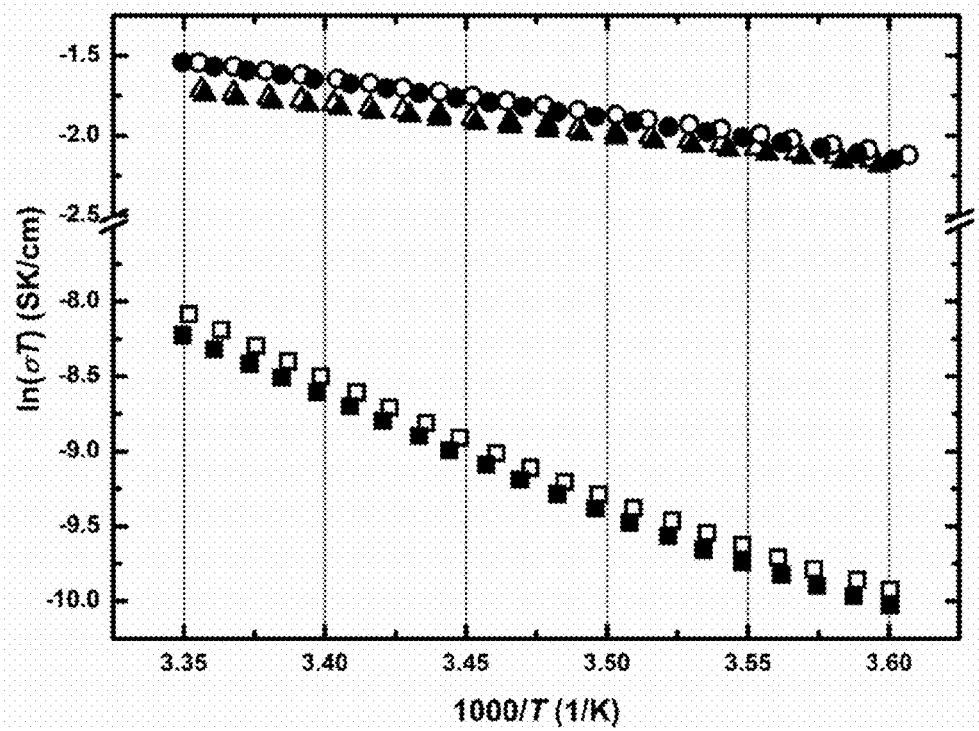

FIG. 5 shows proton conduction in $\{(NH_4)_2[Mn(ina)_4(SCN)_2]\}_n$ a) Arrhenius plots for a (1)→(2)→(3) sequence: (1) as-synthesized (circles); (2) dried for 3 h at 60° C., 25 mbar and kept in air at approx. 40% RH for 4 days (squares); (3) kept over water in a closed vial for 16 h at 40° C. and kept in air at approx. 40% RH for 4 days (triangles). Open and closed symbols denote cooling and heating cycles, respectively.

Figure 6:
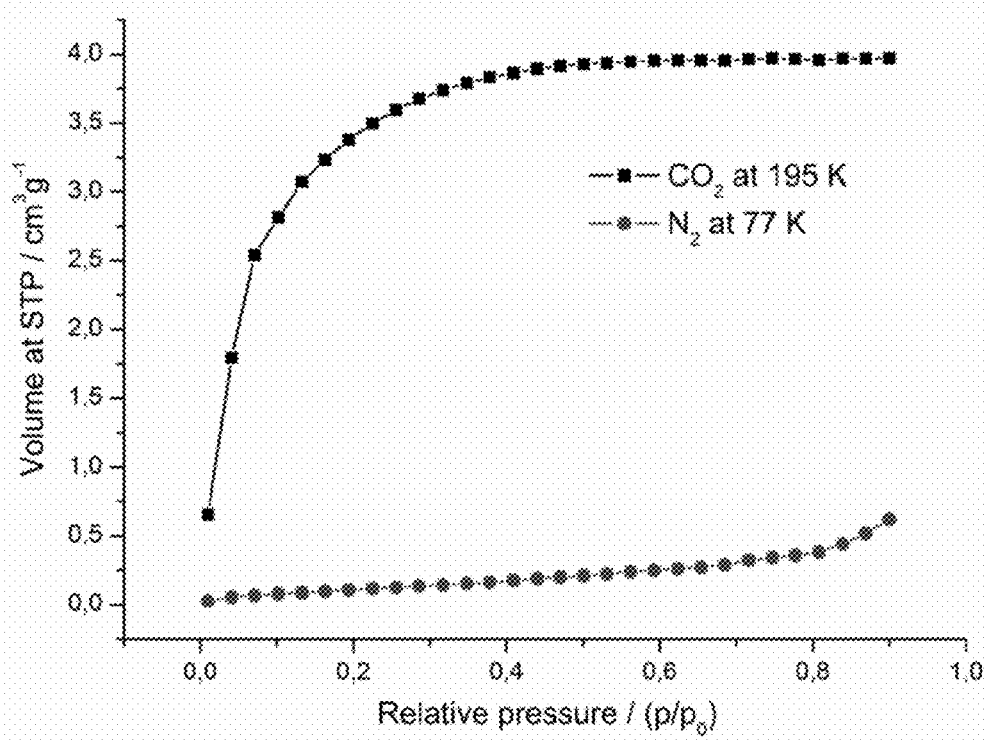

FIG. 6 shows selective $CO_2$ vs $N_2$ adsorption for activated $\{[Mn_2(ina)_4(H_2O)_2].2EtOH\}_n$. $CO_2$ and $N_2$ adsorption isotherms at 195 K and 77 K, respectively.

The invention is illustrated by the following examples not limiting in any way the scope of its protection.

EXAMPLE 1

Compound $\{[Mn_2(ina)_4(H_2O)_2].2EtOH\}_n$, in which (L=$H_2O$; S=EtOH; x=2; y=2).

Isonicotinic acid hydrazide (isoniazid) (274 mg; 2.00 mmol) was dissolved in 92% ethanol (40 mL) containing acetone (700 μL; 10.0 mmol) and was heated under reflux for about 10 minutes. Then 80% acetic acid (215 μL; 3.00 mmol) and $[Mn(CH_3COO)_2].4H_2O$ (245 mg; 1.00 mmol) were added. Refluxing the resulting pale yellow solution was continued for about 10 minutes. Then the solution was left for crystallization. After approximately 6 days dark yellow crystals were filtered, washed with ethanol and dried in air at room temperature. Yield: 200 mg; 55%.

Elemental analysis: Calculated for $C_{28}H_{32}Mn_2N_4O_{12}$: C, 46.29; H, 4.44; N, 7.71. Found: C, 45.99; H, 4.53; N, 7.70%. IR (ATR, cm$^{-1}$): $\nu(COO)_{as}$ 1643 s 1599 vs, $\nu(COO)_s$ 1415 s 1396 vs, $\nu(CO_{etanol})$ 1049 w, $\nu(CH_{etanol})$ 2972 w, $\nu(OH)$ 3271 m br. Magnetic moment (298 K): $\mu_{eff}$=5.7$\mu_B$. Surface area $S_{BET-N2}$=11 m$^2$/g (in −196° C., the average of three, single point measurements for $p/p_0=0.1$; 0.2; 0.3). UV-vis (solid state) λ, nm: 447, 441, 419, 400, 310 sh, 269, 214.

Crystallographic data (SCXRD): monoclinic, space group $P2_1/c$, a=10.869(5), b=12.130(5), c=13.783(4) Å, β=117.75(2°), V=1608.2(11) Å$^3$, T=293(2) K, Z=4, $D_C$=1.500 Mg m$^{-3}$, μ=6.974 mm$^{-1}$, 22994 reflections measured, 3093 reflections unique ($R_{int}$=0.0405), 2776 reflections observed [I>2σ(I)]. $R_1$=0.0329; $wR_2$=0.0832 [for 2776 reflections observed].

Figure 1:
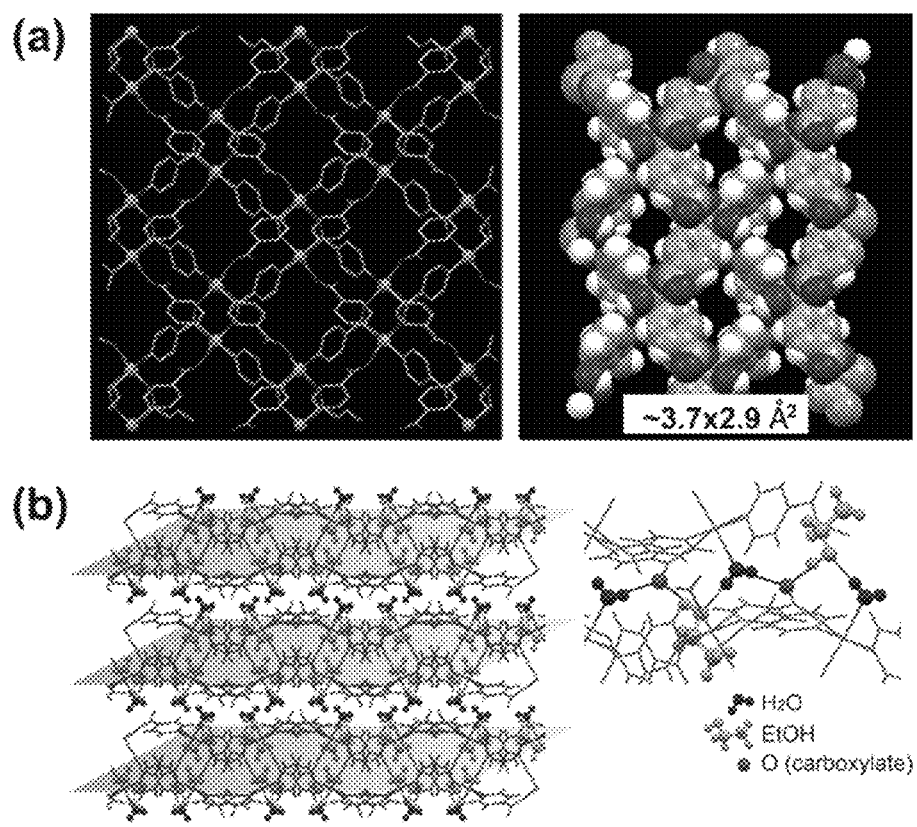

Single-crystal XRD revealed that the isonicotinate ligands in $\{[Mn_2(ina)_4(H_2O)_2].2EtOH\}_n$ function as $μ_3$ and $μ_2$ linkers between the carboxylate-bridged dinuclear $Mn^{II}$ clusters and act as nodes in the layered framework of a (4,4)-topology (FIG. 1). The framework also exhibits 1D channels of approximately 3.7×2.9 Å$^2$, which were occupied by EtOH guest molecules. The non-polar ethyl groups were directed inside the 10.8 Å-thick layers. In contrast, the hydroxyl groups of the ethanol units were involved in strong hydrogen-bonds (O—H . . . O distances range from 2.666 to 2.786 Å) with both the framework free carboxylate groups and coordinated $H_2O$ guest molecules. The structural flexibility of the framework arises from its interlayer hydrogen-bonding acceptor sites and labile guest molecules that can be easily and selectively removed.

Figure 2:
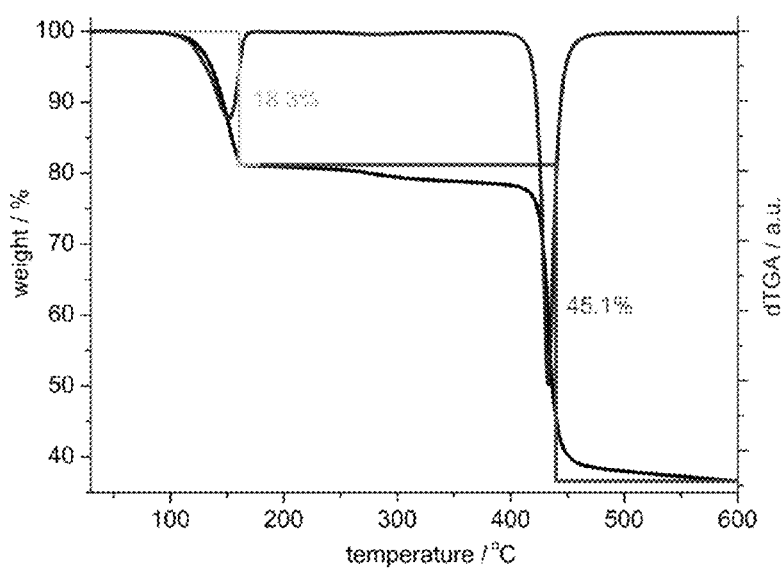
FIG. 2 shows TG and dTG curves for $\{[Mn_2(ina)_4(H_2O)_2].2EtOH\}_n$ showing stepwise weight loss upon heating.

TGA/QMS for $\{[Mn_2(ina)_4(H_2O)_2].2EtOH\}_n$ revealed a stepwise weight loss (FIG. 2) with an approximate plateau in the range 170-400° C., upon heating. The first distinct step with a maximum at 151° C. corresponds to the loss of two solvate ethanol and two coordination water molecules per formula unit (found: 18.3%, m/z=14 [$CH_2$]$^+$, 15 [$CH_3$]$^+$, 17 [OH]$^+$, 18 [$H_2O$]$^+$; calculated weight-loss: 17.6%). The final distinct step occurring at 433° C. was assigned to the loss of carboxylate groups (found: 45.1%, m/z=28 [CO]$^+$, 44 [COO]$^+$) and is associated with a decomposition of the compound.

EXAMPLE 2

Compound $\{[Mn_2(ina)_4(H_2O)_2]\}_n$, in which (L=$H_2O$; x=2; y=0).

Yellow powdered compound $\{[Mn_2(ina)_4(H_2O)_2].2EtOH\}_n$ (101.7 mg; 0.2800 mmol) was heated for approx. 1 hour at 150° C., after that the sample was immediately weighed. Weight loss of 18.3 mg corresponding to the release of two water molecules and two ethanol molecules per one formula unit of $[Mn_2(ina)_4(H_2O)_2].2EtOH$ was observed. The resulting pale yellow powder of $\{[Mn_2(ina)_4]\}_n$ (x=0; y=0) (83.4 mg; 0.279 mmol) was exposed to air for about 1 hour at room temperature. Weight gain of 4.9 g corresponding to the uptake of two water molecules per one unit of $[Mn_2(ina)_4(H_2O)_2].2EtOH$ was observed. The resulting pale yellow powder of $\{[Mn_2(ina)_4(H_2O)_2]\}_n$ was obtained (88.3 mg; 0.278 mmol). Yield: 100%.

Elemental analysis: Calculated for $C_{24}H_{20}Mn_2N_4O_{10}$: C, 45.44; H, 3.18; N, 8.83. Found: C, 45.61; H, 3.10; N, 9.01%. IR (ATR, cm$^{-1}$): ν(COO)$_{as}$ 1609 s, ν(COO)$_s$ 1405 s 1394 vs, UV-vis (solid state) λ, nm: 390 sh, 310 sh, 272, 210.

EXAMPLE 3

Compound $\{[Mn_2(ina)_4].2EtOH\}_n$, in which (x=0; S=EtOH; y=2).

Yellow powdered compound $\{[Mn_2(ina)_4(H_2O)_2].2EtOH\}_n$ (82.7 mg; 0.228 mmol) was placed in a desiccator over $P_4O_{10}$ under reduced pressure (p≈40 hPa) at room temperature for about 24 hours. Weight loss of 4.1 mg corresponding to the release of two water molecules per one formula unit of $[Mn_2(ina)_4(H_2O)_2].2EtOH$ was observed. The resulting yellow powder of $\{[Mn_2(ina)_4].2EtOH\}_n$ was obtained (78.6 mg; 0.228 mmol). Yield: 100%.

$\{[Mn_2(ina)_4].2EtOH\}_n$ was exposed to air for about 1 hour at room temperature. Weight regain of 4.1 g corresponding to the uptake of two water molecules per one unit of $[Mn_2(ina)_4(H_2O)_2].2EtOH$ was observed. The resulting yellow powder of $\{[Mn_2(ina)_4(H_2O)_2].2EtOH\}_n$ was obtained (82.7 mg; 0.228 mmol). Yield: 100%. Compound identification was based on the IR spectrum.

EXAMPLE 4

Modification of $\{[Mn_2(ina)_4(H_2O_2)_2].2EtOH\}_n$ compound with ammonium thiocyanate (by mechanochemical method in LAG variant).

$\{[Mn_2(ina)_4(H_2O)_2].2EtOH\}_n$ compound (80.0 mg; 0.220 mmol) and $NH_4SCN$ (33.5 mg; 0.440 mmol) were ground in an agate mortar at room temperature in air for about 20 minutes in 4 cycles, 5 minutes each. In each cycle approximately 100-120 μL of 92% ethanol was added to the system (mechanochemical method in LAG variant). Light yellow powder of $\{(NH_4)_2[Mn(ina)_4(SCN)_2]\}_n$ was obtained. Yield: 99.4 mg; 100%.

It has been confirmed by IR spectroscopy that after 1 minute of neat grinding (NG) the product is already formed.

Elemental analysis: Calculated for $C_{14}H_{16}N_6O_4S_2Mn$: C, 37.25; H, 3.57; N, 18.62; S, 14.21. Found: C, 36.89; H, 3.51; N, 18.46; S, 14.29%. IR (ATR, cm$^{-1}$): ν(COO)$_{as}$ 1580 vs ν(COO)$_s$ 1408 s, δ(NH)$_{ammonium}$ 1479 m 1437 s, ν(SCN) 2103 vs, ν(NH$_{ammonium}$) 3236 m 3186 m. UV-vis (solid state) λ, nm: 310 sh, 268, 230, 211.

Figure 3:
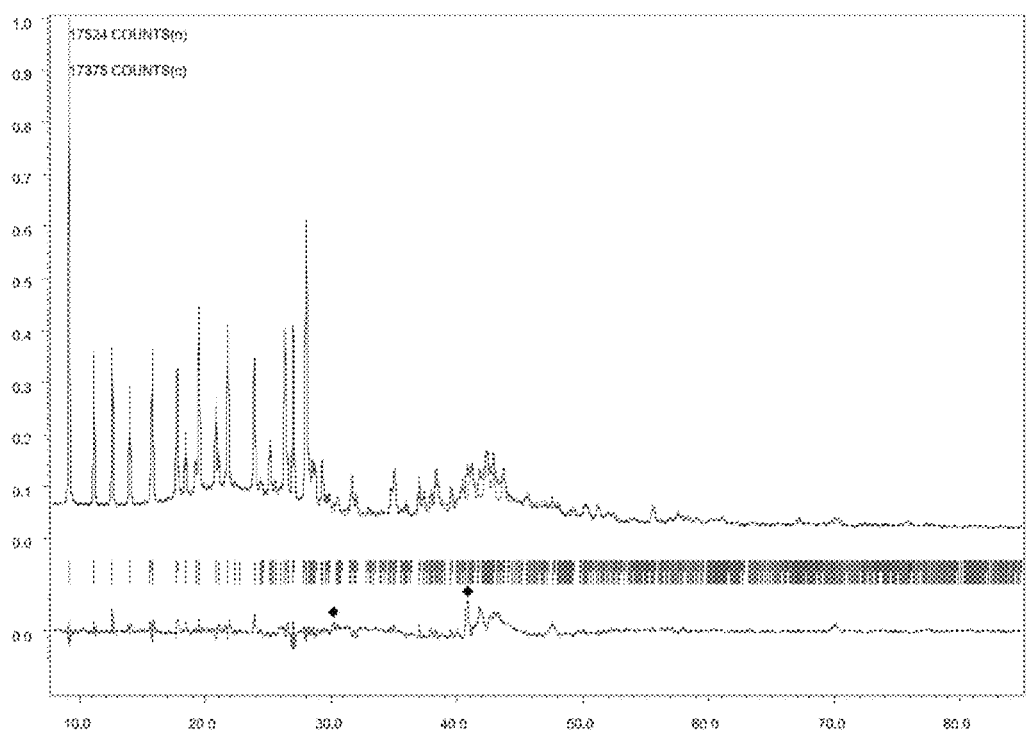
FIG. 3 shows the observed (black line) and calculated (gray line) PXRD patterns of $\{(NH_4)_2[Mn(ina)_4(SCN)_2]\}_n$ along with the difference curve (bottom black line).

Crystallographic data (PXRD): monoclinic, space group $P2_1/c$, a=9.72, b=14.1, c=7.15 Å, β=97.9°, V=968 Å$^3$, T=293 K. The PXRD pattern for the $\{(NH_4)_2[Mn(ina)_4(SCN)_2]\}_n$ is presented on FIG. 3.

The stoichiometry of the reaction (1:2; $\{[Mn_2(ina)_4(H_2O)_2].2EtOH\}_n$ to $NH_4SCN$) as well as the formation of a new, crystalline phase of $\{(NH_4)_2[Mn(ina)_4(SCN)_2]\}_n$ can be detected by IR spectroscopy and powder X-ray diffraction (FIG. 4). Reactions carried out at higher stoichiometries of $NH_4SCN$ give mixtures of the thiocyanate and $\{(NH_4)_2[Mn(ina)_4(SCN)_2]\}_n$, whereas all reactions with lower stoichiometry of $NH_4SCN$ lead to mixtures of the unreacted $\{[Mn_2(ina)_4(H_2O)_2].2EtOH\}_n$ and $\{(NH_4)_2[Mn(ina)_4(SCN)_2]\}_n$, whose amount is limited by the thiocyanate.

EXAMPLE 5

Proton conductivity of $\{(NH_4)_2[Mn(ina)_4(SCN)_2]\}_n$ compound.

The proton conductivity of $\{[Mn_2(ina)_4(H_2O)_2].2EtOH\}_n$ and $\{(NH_4)_2[Mn(ina)_4(SCN)_2]\}_n$ was evaluated by AC 4-probe method performed on powdered sample pressed between two gold electrodes in a sealed glass tube within temperature range +5° C. and +30° C. $\{[Mn_2(ina)_4(H_2O)_2].2EtOH\}_n$, precursor of $\{(NH_4)_2[Mn(ina)_4(SCN)_2]\}_n$, was not conductive, i.e. the conductivity was lower than S<10$^{-7}$ S cm$^{-1}$. However, the proton conductivity of as-synthesized $\{(NH_4)_2[Mn(ina)_4(SCN)_2]\}_n$ was found to be 7.0×10$^{-4}$ S cm$^{-1}$ at 25° C., estimated from the linear fit of the Arrhenius plot in FIG. 5. This proton conductivity is among the highest reported for MOFs so far ((a) Ramaswamy, P.; Wong, N. E.; Shimizu, G. K. H. *Chem. Soc. Rev.* 2014, 43, 5913. (b) Horike, S.; Umeyama, D.; Kitagawa, S. *Acc. Chem. Res.* 2013, 46, 2376-2384. (c) Yoon, M.; Suh, K.;

Natarajan, S.; Kim, K. *Angew. Chem. Int. Ed.* 2013, 52, 2688). To gain more insight into the conducting process, the sample of $\{(NH_4)_2[Mn(ina)_4(SCN)_2]\}_n$ was dried and then stepwise humidified. It has been observed that the dried sample (3 h at 60° C., 25 mbar) was not conductive (S<$10^{-7}$ S cm$^{-1}$). This finding indicates the presence of interlayer water molecules that play an important role in creating the proton-conducting pathways in $\{(NH_4)_2[Mn(ina)_4(SCN)_2]\}_n$ (the formula of the compound may also be presented as $\{(NH_4)_2[Mn(ina)_2(NCS)_2]\}_n \cdot xH_2O$). These water molecules ($xH_2O$) are adsorbed on its layers and disordered, and as such cannot be included in the X-ray crystal structure, elucidated from the PXRD data. On the other hand, when the dried sample was conditioned in air at approx. 40% RH (relative humidity), only a partial restoration ($1.2 \times 10^{-6}$ S cm$^{-1}$ at 25° C.) of conductivity was observed (FIG. 5). In contrast, when this sample was further exposed to 100% RH followed by conditioning at approx. 40% RH, its degree of hydration was (FIG. 5). Both the reversibility of proton conductivity property as well as the stability under high humidity extending to soaking in water, are desirable features of $\{(NH_4)_2[Mn(ina)_4(SCN)_2]\}_n$ in the context of its fuel cells applications.

The Arrhenius plots of the proton conductivity allow for calculation of the activation energy ($E_a$) for $\{(NH_4)_2[Mn(ina)_4(SCN)_2]\}_n$ samples. The obtained value of 0.20 eV for the as-synthesized material indicates the Grotthuss mechanism of proton conduction involving rotational movements of $NH_3/NH_4^+$ and $H_2O/H_3O^+$ moieties (Kreuer K.-D.; Rabenau A.; Weppner *Angew. Chem. Int. Ed.* 1982, 21, 208). In contrast, the sample with partially recovered hydration and resulting restored conductivity exhibits higher $E_a$=0.64 eV suggesting that proton conduction in $\{(NH_4)_2[Mn(ina)_4(SCN)_2]\}_n$ includes another process involving translational movements of the aforementioned molecules/ions (vehicle mechanism).

EXAMPLE 6

$CO_2$ and $N_2$ adsorption isotherms for activated $\{[Mn_2(ina)_4(H_2O)_2] \cdot 2EtOH\}_n$ (FIG. 6)

$\{[Mn_2(ina)_4(H_2O)_2] \cdot 2EtOH\}_n$ was degassed at 150° C. for 1 hour prior to analysis. Measurements were performed in triplicates on degassed samples at 195K ($CO_2$) and 77K ($N_2$) over a pressure range of 0.01-0.90 bar. The data reflects the average volumes at STP (cm$^3$/g).

The invention claimed is:

1. A layered MOF-type coordination polymer of manganese defined by the general formula 1:

$$\{[Mn_2(ina)_4(L)_x] \cdot yS\}_n$$
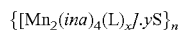

in which:
ina is an isonicotinic acid anion;
L is a neutral molecule of a solvent selected from the group consisting of $C_1$-$C_{12}$ alcohols or water;
S independently denotes inert solvent molecule selected from the group consisting of $C_1$-$C_{12}$ alcohols or water;
x varies from 0 to 2;
y Independently varies in the range from 0 to 4;
n denotes a polymeric structure of the general formula, wherein the layered MOF-type coordination polymer is a two-dimensional network.

2. The layered polymer according to claim 1, characterized in that L means water, S is ethanol, x=2, y=2.

3. The layered polymer according to claim 1, characterized in that L means water, x=2, y=0.

4. The layered polymer according to claim 1, characterized in that S is ethanol, x=0, y=2.

5. The layered polymer according to claim 1, characterized in that x=0, y=0.

6. A method for producing the layered MOF-type coordination polymer of claim 1, characterized in that isonicotinic acid hydrazide is condensed through a condensation reaction with a lower ketone or aldehyde under anaerobic or aerobic conditions or in air, wherein the condensation reaction is carried out at 1:1 molar ratio of an aldehyde or ketone with isoniazid or at a stoichiometric excess of one of the reactants, in a $C_1$-$C_{12}$ alcohol or aqueous-alcoholic solution, formed by mixing of $C_1$-$C_{12}$ alcohol and water in any ratio, and in a second stage to prevent the deprotonation of the resulting hydrazide-hydrazone, an acidic substance and a salt of manganese(II) are added, wherein the second stage is carried out at a molar ratio 1:2:2 of manganese to isoniazid to acid or at a stoichiometric excess or a deficiency of the acid.

7. The method according to claim 6, characterized in that, as a manganese(II) salt, manganese(II) actetate hydrated or anhydrous is used.

8. The method according to claim 6, wherein the method is carried out in the temperature range of −130° C. to 260° C. and in the pressure range of 0.01 to 1 MPa.

9. The method according to claim 6 characterized in that as a factor preventing hydrazide-hydrazone deprotonation, acetic acid is used.

10. The method according to claim 6 characterized in that the resulting compounds are heated to temperatures not exceeding 400° C. and/or subjected to reduced pressure and/or contacted with a strong dehydrating agent in the form of phosphorus pentoxide $P_4O_{10}$.

11. A method of modifying the layered MOF-type coordination polymer of claim 1 by with an ionic substance to form a modified compound characterized in that the modifying is carried out by grinding of the layered MOF-type coordination polymer in a mortar or a ball mill with the ionic substance without solvent or with addition of solvent in an amount of up to 10 µl per 1 mg of solid reactants (liquid-assisted grinding method), wherein grinding in a mortar or ball mill is carried out at a molar ratio of the coordination polymer to the ionic substance in the range from 10:1 to 1:10, and in the case of using LAG method (liquid-assisted grinding method), solvent is eventually removed by evaporation which occurs during the grinding.

12. The method according to claim 11 characterized in that as a solvent in the LAG method $C_1$-$C_{12}$ alcohol or aqueous-alcoholic solution formed by mixing $C_1$-$C_{12}$ alcohol and water in any ratio, is used.

13. The method according to claim 11 characterized in that the modifying with addition of solvent is carried out at a molar ratio of the coordination polymer to the ionic substance in the range from 100:1 to 1:100, wherein the modifying is carried out in the temperature range of −130° C. to 260° C. and in the pressure range of 0.01 to 1 MPa.

14. The method according to claim 11 wherein the solvent is pyridine, N,N-dimethylformamide, N,N-diethylformamide, N,N-imethylacetamide, dimethyl sulfoxide, N-methylpyrrolidone, dimethyl carbonate, diethyl carbonate, $C_1$-$C_{12}$ alcohols, water, halogenated alkanes, acetonitrile, tetrahydrofuran or mixtures thereof.

15. The method according to claim 11 wherein the ionic substance is a compound containing at least one anion from the group: halides (fluorides, chlorides, bromides, iodides), hydroxides, nitrates, sulfates, bisulfates, thiosulphates, phosphates, hydrophosphates, carbonates, bicarbonates, chlorates, bromates, iodates, thiocyanates, cyanides, cyanates, chromates, dichromates, silicates, arsenates, acetates, formates, oxalates, citrates, sulfides, hexafluorophosphates, tetrafluoroborates, tetraphenylborates, molybdates, tungstates, vanadates, phthalates, hydrogen phthalates, terephthalates, and containing at least one cation from the group: ammonium, alkylammonium, hydrogen, lithium, sodium, or potassium.

16. A method for detecting, capture, separating or storage of a molecule comprising contacting the layered MOF-type manganese coordination polymer of claim 1 with the molecule to form a modified compound.

17. The method according to claim 11 characterized in that the modified compound is used for the preparation of superionic or ionic-electronic conductors, or for construction of batteries, supercapacitors or fuel cells.

18. The method of claim 16, wherein said molecule is hydrogen, carbon dioxide, carbon monoxide, an alcohol, water, or a hydrocarbon or any combination thereof.

* * * * *